(12) United States Patent
Ostepchuk

(10) Patent No.: US 12,569,366 B2
(45) Date of Patent: Mar. 10, 2026

(54) APPARATUS AND METHOD FOR ENHANCING PHYSIOLOGICAL THERMOREGULATION

(71) Applicant: Braeden Ostepchuk, Voorhees, NJ (US)

(72) Inventor: Braeden Ostepchuk, Voorhees, NJ (US)

( * ) Notice: Subject to any disclaimer, the term of this patent is extended or adjusted under 35 U.S.C. 154(b) by 234 days.

(21) Appl. No.: 18/375,373

(22) Filed: Sep. 29, 2023

(65) Prior Publication Data

US 2024/0058164 A1    Feb. 22, 2024

Related U.S. Application Data

(63) Continuation-in-part of application No. 17/889,215, filed on Aug. 16, 2022, now Pat. No. 11,808,493.

(51) Int. Cl.
*A61F 7/00*            (2006.01)
(52) U.S. Cl.
CPC ........ *A61F 7/00* (2013.01); *A61F 2007/0036* (2013.01); *A61F 2007/0063* (2013.01); *A61F 2007/0095* (2013.01)
(58) Field of Classification Search
CPC .................. F25B 21/02; F25B 2321/02; F25B 2321/0212; F25B 2700/2107; F28D 15/0275; H10N 10/13
See application file for complete search history.

(56) References Cited

U.S. PATENT DOCUMENTS

| | | | | |
|---|---|---|---|---|
| 10,634,397 | B2 * | 4/2020 | Fisher | F28D 15/0266 |
| 10,660,534 | B2 * | 5/2020 | Lee | A61B 5/02438 |
| 10,675,177 | B2 * | 6/2020 | Vogel | F25D 3/08 |
| 11,162,716 | B2 * | 11/2021 | Alexander | A01N 1/148 |
| 11,333,562 | B1 * | 5/2022 | Johnson | G01K 13/20 |
| 11,547,312 | B2 * | 1/2023 | Wang | G04G 21/025 |
| 11,801,423 | B2 * | 10/2023 | Bissonnette | A63B 23/1209 |
| 11,887,717 | B2 * | 1/2024 | Rosenberg | G16H 20/30 |
| 12,042,426 | B2 * | 7/2024 | Breiter | A61F 7/007 |
| 2019/0053713 | A1 | 2/2019 | Debates | |
| 2019/0254866 | A1 * | 8/2019 | Whiteley | A61M 19/00 |
| 2019/0277544 | A1 * | 9/2019 | Lakshmanan | B60N 2/58 |
| 2019/0365253 | A1 | 12/2019 | Rytky | |
| 2020/0343433 | A1 | 10/2020 | Boukai | |
| 2021/0219736 | A1 * | 7/2021 | Youngblood | A47C 21/048 |
| 2021/0262680 | A1 * | 8/2021 | Zhao | F24F 11/57 |
| 2021/0282472 | A1 | 9/2021 | Gueritee | |
| 2021/0315731 | A9 | 10/2021 | Smith | |
| 2022/0352452 | A1 * | 11/2022 | Tanaka | H10N 10/10 |

* cited by examiner

*Primary Examiner* — Filip Zec
(74) *Attorney, Agent, or Firm* — CALDWELL LLC

(57) ABSTRACT

An apparatus and method for enhancing physiological thermoregulation, the apparatus including a housing configured to contact a glabrous area of a user, wherein the housing includes a cooling element; and a plurality of sensors configured to generate a biometric datum; at least a processor communicatively connected to the plurality of sensors; and a memory communicatively connected to the at least processor, the memory containing instructions configuring the at least processor to receive the biometric datum from the plurality of sensors; and control the cooling element as a function of the biometric datum.

20 Claims, 9 Drawing Sheets

500

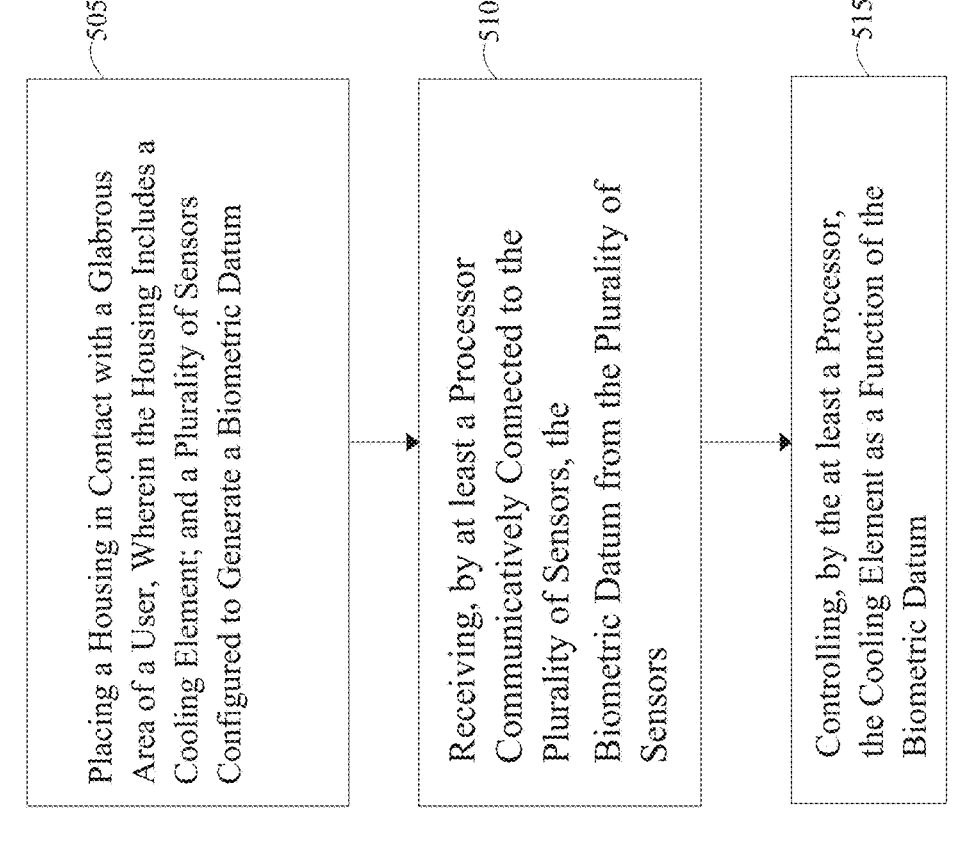

Placing a Housing in Contact with a Glabrous Area of a User, Wherein the Housing Includes a Cooling Element; and a Plurality of Sensors Configured to Generate a Biometric Datum ⟋505

Receiving, by at least a Processor Communicatively Connected to the Plurality of Sensors, the Biometric Datum from the Plurality of Sensors ⟋510

Controlling, by the at least a Processor, the Cooling Element as a Function of the Biometric Datum ⟋515

*FIG. 5*

APPARATUS AND METHOD FOR ENHANCING PHYSIOLOGICAL THERMOREGULATION

CROSS-REFERENCE TO RELATED APPLICATIONS

This application is a continuation-in-part of Non-provisional application Ser. No. 17/889,215 filed on Aug. 16, 2022, and entitled "APPARATUS AND METHOD FOR ENHANCING PHYSIOLOGICAL THERMOREGULATION," the entirety of which is incorporated herein by reference.

FIELD OF THE INVENTION

The present invention generally relates to the field of physiological thermoregulation. In particular, the present invention is directed to an apparatus and method for enhancing physiological thermoregulation.

BACKGROUND

All biological processes operate in narrow thermal ranges; even small variations in temperature may lead to performance degradation and/or cellular/systemic failure. Research shows that performance degradation (fatigue, muscular failure) is most likely attributed to the suppression the nervous system due to core temperature, rather than the accumulation of lactic acid, poor oxygen supply, or limited availability of glycogen. As core temperature rises, the nervous system downregulates physiological systems (e.g. neuromuscular activation). There is a need for technology to increase human performance potential and heat stress resilience by enhancing physiological thermoregulation.

SUMMARY OF THE DISCLOSURE

In an aspect, an apparatus for enhancing physiological thermoregulation, the apparatus including a housing having an ergonomic contour and configured to contact a glabrous area of a hand of a user; a cooling element including a thermoelectric cooler; and a plurality of sensors configured to receive a biometric datum and an initial exercise datum; at least a processor communicatively connected to the plurality of sensors; and a memory communicatively connected to the at least processor, the memory containing instructions configuring the at least processor to: receive the biometric datum and the initial exercise datum from the plurality of sensors; determine a biometric threshold using a machine learning model and the biometric datum as an input to the machine learning model; control the cooling element as a function of the determined biometric threshold; receive a subsect exercise datum from the plurality of sensors; and generate an improvement datum based on the subsequent exercise datum.

In another aspect, A method for enhancing physiological thermoregulation, the method including placing a housing in contact with a glabrous area of a user, wherein the housing includes; a cooling element including a thermoelectric cooler; and a plurality of sensors configured to receive a biometric datum and an initial exercise datum; receiving, by at least a processor, the biometric datum and the initial exercise datum from the plurality of sensors; determining, by the at least a processor, a biometric threshold using a machine learning model and the biometric datum as an input to the machine learning model; controlling, by the at least a processor, the cooling element as a function of the determined biometric threshold; receiving, by the at least a processor, a subsect exercise datum from the plurality of sensors; and generating, by the at least a processor, an improvement datum based on the subsequent exercise datum.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 5 is a flow diagram of an exemplary method for enhancing physiological thermoregulation;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for enhancing physiological thermoregulation. In an embodiment, the apparatus may include a wearable device to regulate the temperature of a glabrous area of a user.

Aspects of the present disclosure may also be used function as an interface between the human body and the ambient environment, increasing the rate and capacity of heat transfer through the apparatus. Exemplary embodiments illustrating aspects of the present disclosure are described below in the context of several specific examples.

Figure 1:
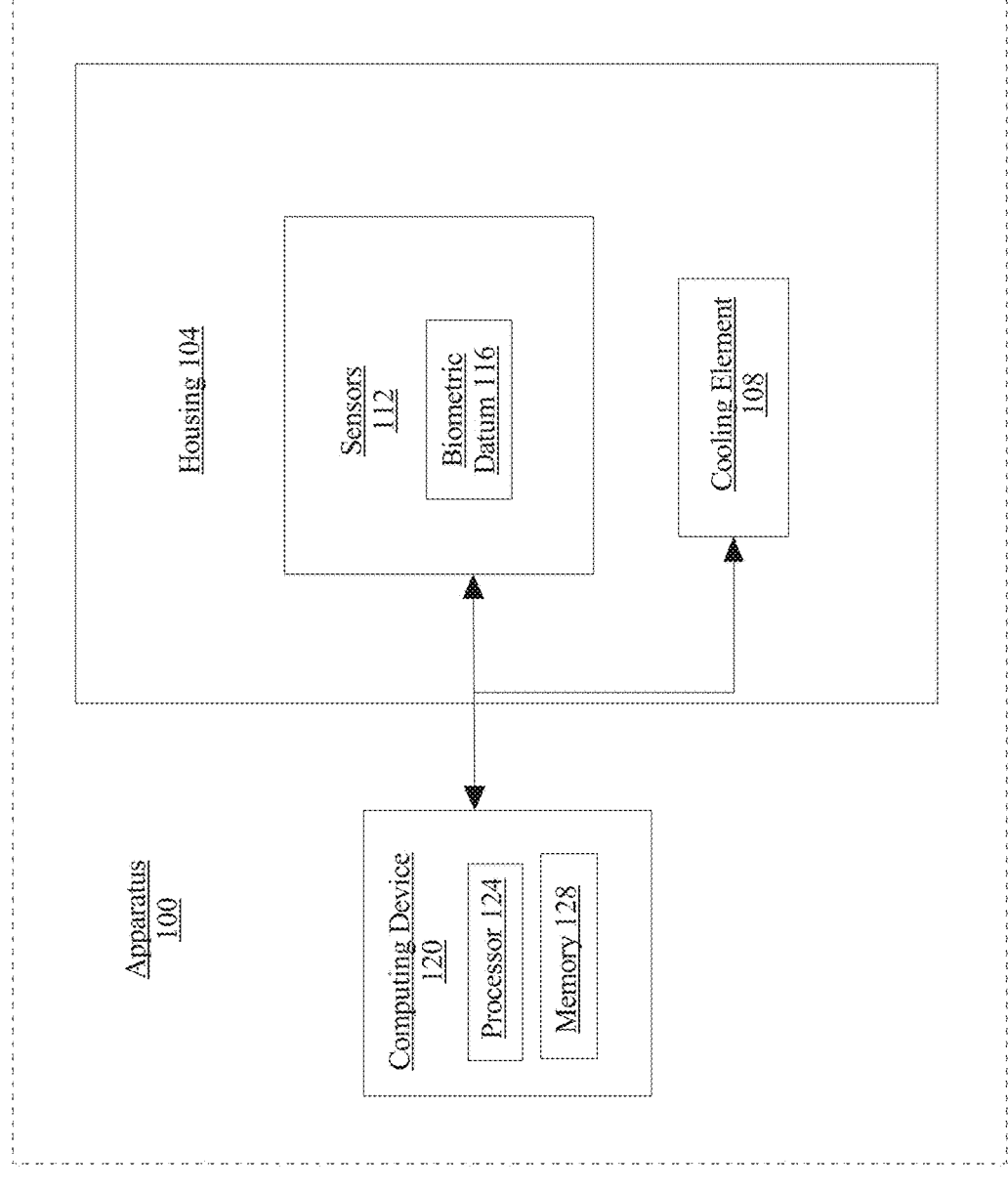
FIG. 1 is an exemplary embodiment of an apparatus for enhancing physiological thermoregulation.

Referring now to FIG. 1, an exemplary embodiment of apparatus 100 for enhancing physiological thermoregulation is illustrated. Apparatus 100 includes a housing 104 in contact with a glabrous area of a user. For the purposes of this disclosure, a first object and a second object are "in contact" if the first object touches the second object. As a nonlimiting example, housing 104 may be in contact with a glabrous area of the user when the user wraps their hand around housing 104, such that housing 104 is in contact with the palm of the user. In some embodiments, housing 104 may be mechanically attached to a glabrous area of a user. "Physiological thermoregulation," as used in this disclosure, is a mechanism by which mammals regulate body temperature in response to an environment. A "housing," as used in this disclosure, is a structure containing a plurality of devices. A "user," as used in this disclosure is a person. A person may be someone wearing or utilizing apparatus 100. A "glabrous area," as used in this disclosure, is an interface on a body characterized by a lack of hair follicles and dense vasculature of arteriovenous anastomoses (AVAs) which enable extremely high rates of heat transfer. "Mechanically attached," as used in this disclosure, is the attachment of at least a portion of apparatus to at least a portion of a user via mechanical coupling. Mechanical coupling may include, for example, materials such as hooks, loops, buckles, buttons, zippers, rope, straps, lace, string, VELCRO, hook-and-loop, or similar material to attach at least a portion of apparatus 100 to a glabrous area of user. Said materials, may be used to at least secure the housing 104 of apparatus 100 to a body part of a user. In some embodiments, mechanical coupling material may be a part of the outer housing of apparatus 104. For example, a VELCRO strap may be used to secure apparatus 100 around the wrist of a user. In another example, apparatus 100 may be tied to the foot of a user using shoelace and loops. The user may have a plurality of glabrous areas. The glabrous areas may include the palms of the hand, soles of the feet, and the upper face. In some embodiments, housing 104 may include a hard or a soft exterior made from material such as nickel, chromium, stainless steel, and/or aluminum alloy. Housing 104 may include an ergonomic shape for maximum conductive heat transfer. As used in this disclosure, an "ergonomic shape," is a shape that is designed for efficiency and comfort in a working environment. An ergonomic shape may be a design that is focused on people and how they might interact with something in a working environment. A "working environment," as used in this disclosure, is an environment where a user may physically exert a glabrous area of the body. Physical exertion may include lifting objects, walking, typing, and similar activities. For example, the ergonomic shape of housing 104 as handwear may include housing 104 being designed to maximize outer protection and finger dexterity. In some embodiments, housing 104 may include a hand grip, so that housing 104 is more comfortable for a user to hold. In some embodiments, hand grip may also serve to increase contact with a user's hand, thereby increasing thermal conductivity. In some embodiments, housing 104 may be made out of or incorporate flexible material that may mold housing 104 to into personalized ergonomic shape fitting the user. In some embodiments, housing 104 may include poly-urethane, latex, nitrile and similar components in the form of gel, foam, or any other form that allow for ergonomic shape. For example, housing 104 designed as a glove.

In a further embodiment, with continued reference to FIG. 1, apparatus 100 may include a housing 104 having an ergonomic contour and configured to contact glabrous area of a hand of a user. As used in this disclosure, an "ergonomic contour" refers to a design shape or form which is intended to comfortably fit or conform to the human hand, thereby promoting ease of use and minimizing user discomfort during prolonged usage. Ergonomic design may ensure a close and effective contact with glabrous area. In another embodiment, housing 104 may include a grip designed to be held by the user. the grip may feature a textured surface, ensuring that the user can maintain a secure hold on apparatus 100, even if conditions are wet or sweaty. Additionally, housing 104 may include at least one groove extending along its outer surface, providing an intentional placement for the fingers of the user for added stability. As a non-limiting example. As a non-limiting example, this groove may be strategically placed along the side of housing 104 to accommodate the natural positioning of the user's fingers, allowing for intuitive grasping and reducing the likelihood of slippage. This design may further enhance the user's experience and ensures apparatus remains securely in place, optimizing its performance in varying conditions.

Still referring to FIG. 1, housing 104 may include a geometric composition similar to that of handwear, foot-wear, or headwear. For example, gloves, socks, mittens, headbands, bracelets, watches, rings, glasses, face masks, handheld devices (e.g., phones, gaming consoles, cups, office equipment, computer mouse, keyboard, chair armrest, stress ball, pens, pencils, etc.), headsets (e.g., virtual reality headsets, headphones, etc.) shoes, hats, and similar forms of hand, foot, and the like. In some embodiments, housing 104 may include a geometric composition similar to handles. A "handle," as used in this disclosure, is part of, or attachment to, an object that allows it to be grasped and manipulated by hand or foot. Handles may include handlebars such as drop handlebars, uprights handlebars, riser handlebars, barbells, hand grips, dumbbells, exercise equipment handlebars. Handles may include hand knobs, such as doorknobs, squeeze bulbs, dynamometers, stress balls, exercise balls, medical equipment (e.g. blood pressure monitors, etc.), and similar equipment. In some embodiments, the handle may be attached equipment such as exercise and medical equipment. For example. A handlebar may be attached to a bike and a handgrip may be attached to a dynamometer. In some embodiments, handles may include foot handles such as foot pedals, scales, and the like.

Still referring to FIG. 1, housing 104 includes a cooling element. A "cooling element," as used in this disclosure, is a device configured to regulate the temperature of a glabrous are of a user. In some embodiments, cooling element 108 may be a device configured to reduce the temperature of a glabrous area of a user by heat transfer through housing 104. In some embodiments, cooling element 108 may be a device configured to increase the temperature of a glabrous area of a user by heat transfer through housing 104. Cooling element 108 may be mechanically attached to the outer of housing 104 or integrated into housing 104. Cooling element 108 may include a or a plurality of heatsinks. A "heatsink," as used in this disclosure, is a heat exchanger that transfers heat from the apparatus to a fluid medium. A fluid medium may include, as non-limiting examples air, water, liquid coolant, and the like. In some embodiments, heatsink may transfer heat from the user to the fluid medium. For example, in some embodiments, heatsink male be in thermal communication with the glabrous area of the user. For the purposes of this disclosure, "thermal communication," means that components are connected such that heat can be transferred between them. In some embodiments, heatsink may transfer heat from another component of cooling element 108 to a fluid medium. For example, in embodiments where cooling element 108 include a thermoelectric cooler, a heatsink may help transfer heat from the "hot" side of the thermoelectric cooler to a fluid medium. In some embodiments, the heat-sink may be in thermal communication with other compo-nents of cooling element 108. A heatsink may be made from a material with high heat transfer abilities and/or high thermal conductivity. As a non-limiting example, a heatsink may include aluminum. As another non-limiting example, a heatsink may include copper. In some embodiments, a heatsink may include a fin or a pin design for maximum surface area and air flow. For example, a pin-fin heat sink may have pins that extend from its base. The pins may be cylindrical, elliptical or square. In some embodiments, cooling element 108 may include a thermoelectric cooler. As a non-limiting example, a pin-fin heat sink may have pins that extend from its base. The pins may be cylindrical, elliptical, or square. A pin-fin heat sink arrangement may include a straight fin. These fins may run the entire length of the heat sink. A variation on the straight-fin heat sink may include a cross-cut heat sink. A straight-fin heat sink may be cut at regular intervals. A heatsink may be configured to lower the temperature of the housing using convective heat transfer. In some embodiments, cooling element 108 may include a fan. Additionally, a heatsink may be connected to a fan adapted for use with a heatsink. The fan may be configured to pull or push air over the heat sink in order to increase the convective cooling ability of the heatsink. Cooling element 108 may include a variety of materials. As nonlimiting examples, cooling element 108 may include steel, aluminum, and/or titanium. Materials with a high thermal conductivity are preferred. As nonlimiting examples, cooling element 108 may comprise aluminum and/or copper. In some embodiments, cooling element 108 may comprise a thermally anisotropic material. For the purposes of this disclosure, "thermally anisotropic material" is a material that has different thermal properties in different directions. As a non-limiting example, cooling element 108 may include carbon fiber. Carbon fiber has a higher thermal conductivity along the fibers of the carbon fiber than it has across the fibers of the carbon fiber. In some embodiments, where cooling element 108 comprises carbon fiber, the carbon fiber may be arranged such that the fibers of the carbon fiber are in the direction of the desired flow of heat.

Still referring to FIG. 1, cooling element 108 may additionally include an internal copper heat exchanger and/or integrated copper heat pipe. "Heat exchangers," as used in this disclosure, are devices that transfer heat to achieve desired heating or cooling. A "heat pipe," as used in this disclosure, is a heat-transfer device that employs phase transition to transfer heat between a user and the device. Copper may have many desirable properties for thermally efficient and durable heat exchangers and/or heat pipes. Copper may exhibit high thermal conductivity which may allow heat to pass through housing 104 quickly. A copper heat exchanger and/or copper heat pipe may provide in apparatus 100 corrosion resistance, biofouling resistance, maximum allowable stress and internal pressure, creep rupture strength, fatigue strength, hardness, thermal expansion, specific heat, antimicrobial properties, tensile strength, yield strength, high melting point, alloy, ease of fabrication, and ease of joining.

In some embodiments, heat exchangers and/or heat pipes may be used for thermoelectric cooling. Thermoelectric cooling uses the Peltier effect to create a heat flux at the junction of two different types of materials. A Peltier cooler, heater, or thermoelectric heat pump is a solid-state active heat pump which transfers heat from one side of the device to the other, with consumption of electrical energy, depending on the direction of the current. Such an instrument is also called a Peltier device, Peltier heat pump, solid state refrigerator, or thermoelectric cooler (TEC) and occasionally a thermoelectric battery. It can be used either for heating or for cooling, it can also be used as a temperature controller that either heats or cools. Heat pipes may include, Vapor chambers (planar heat pipes), Variable conductance heat pipes (VCHPs), Pressure controlled heat pipes (PCHPs), Diode heat pipes, Thermosyphons, and Rotating heat pipes. In some embodiments, cooling element 108 may be battery powered. This may include the use of lithium batteries and other rechargeable batteries such as, NiCd (Nickel-Cadmium), NiMH (Nickel-Metal Hydride) and Li-ion (Lithium Ion).

Still referring to FIG. 1, housing 104 includes a plurality of sensors 112 configured to generate a biometric datum. "Biometric datum," as used in this disclosure, is measurements of physical characteristics of a user. Biometric datum 116 may include a user's heart rate, oxygen levels, blood pressure, exertion level, body temperature, temperature datum relating to the glabrous areas of the user, and the like. In some embodiments, Biometric datum 116 may include the temperature of the glabrous area of the as user, such as the palm of a hand. In some embodiments, Biometric datum 116 may include the ambient temperature of areas within housing 104. Processor 124 is configured to receive biometric datum 116 from the plurality of sensors.

With continued reference to FIG. 1, the plurality of sensors 112 may be mechanically attached or integrated into housing 104. The plurality of sensors 112 may include temperature sensors, skin sensors, biometric sensors, accelerometers, blood flow sensors, heat flux sensors and the like. For example, sensors 112 may include, negative temperature coefficient (NTC) thermistors, resistance temperature detectors (RTDS), thermocouples, type k thermocouples, semiconductor-based sensors, infrared sensors, bimetallic devices, thermometers, change-of-state sensors, silicon diode sensors, lambda sensors, blood pressure sensors, accelerometers, gyroscopes, magnetometers, electrochemical biosensors, potentiometric biosensors, optical biosensors, sweat sensors, optical sensors (PPG), microprocessor (PCB) and similar devices capable of identifying biometric datum 116. In an embodiment, a plurality of sensors may be configured to track the user's fitness by detecting an exercise datum. "Exercise datum," as used in this disclosure, is a datum that summarizes the user's overall fitness. Overall fitness may include level of exercises such as counting steps and workouts. Exercise datum may include the intensity, duration, and type of activity a user participates in. Exercise datum may be biometric datum received during a physical activity. For example, heavy weightlifting for an hour on a daily basis. Apparatus 100 may monitor the user heart rate, blood pressure, body temperature, and the like to gage the exertion level and intensity of the workout as exercise datum. In some embodiments, exercise datum and biometric datum may be received by apparatus 100 through user input. "User input," as used in this disclosure, is data inputted by a user. For example, a user input may be received from a user database communicatively connected to apparatus 100 for apparatus 100 to receive. A "user database," as used in this disclosure is a data structure containing user inputs. In some embodiments, machine-learning training data may be received from the user database as described further below. User database may be implemented, without limitation, as a relational user database, a key-value retrieval user database such as a NOSQL user database, or any other format or structure for use as a user database that a person skilled in the art would recognize as suitable upon review of the entirety of this disclosure. User database may alternatively or additionally be implemented using a distributed data storage protocol and/or data structure, such as a distributed hash table or the like. User database may include a plurality of data entries and/or records as described above. Data entries in a user database may be flagged with or linked to one or more additional elements of information, which may be reflected in data entry cells and/or in linked tables such as tables related by one or more indices in a relational user database. Persons skilled in the art, upon reviewing the entirety of this disclosure, will be aware of various ways in which data entries in a user database may store, retrieve, organize, and/or reflect data and/or records as used herein, as well as categories and/or populations of data consistently with this disclosure. In some embodiments, apparatus 100 may calculate biometric and exercises datum in tandem with user input. For example, a user may input, into a graphical user interface, as described further below, that they run 5*k* every day, apparatus 100 may take the user input and use sensors 112 to calculate biometric 116 and exercise datum correlated specifically to the daily 5*k* run.

Still referring to FIG. 1, apparatus 100 includes a computing device 120. Computing device may be configured to control cooling element 108. Computing device 120 includes a processor 124 and a memory 128 communicatively connected to the processor 124, wherein memory 128 contains instructions configuring processor 124 to control cooling element 108 as a function of the biometric datum. Computing device 120 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 120 may include a single computing device operating independently, or may include two or more computing device operating in concert, in parallel, sequentially or the like; two or more computing devices may be included together in a single computing device or in two or more computing devices. Computing device 120 may interface or communicate with one or more additional devices as described below in further detail via a network interface device. Network interface device may be utilized for connecting computing device 120 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 120 may include but is not limited to, for example, a computing device or cluster of computing devices in a first location and a second computing device or cluster of computing devices in a second location. Computing device 120 may include one or more computing devices dedicated to data storage, security, distribution of traffic for load balancing, and the like. Computing device 120 may distribute one or more computing tasks as described below across a plurality of computing devices of computing device, which may operate in parallel, in series, redundantly, or in any other manner used for distribution of tasks or memory between computing devices. Computing device 120 may be implemented using a "shared nothing" architecture in which data is cached at the worker, in an embodiment, this may enable scalability of apparatus 100 and/or computing device.

With continued reference to FIG. 1, computing device 120 may be designed and/or configured to perform any method, method step, or sequence of method steps in any embodiment described in this disclosure, in any order and with any degree of repetition. For instance, computing device 120 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 120 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, additionally, computing device 120 may perform determinations, classification, and/or analysis steps, methods, processes, or the like as described in this disclosure using machine learning processes. A "machine learning process," as used in this disclosure, is a process that automatedly uses a body of data known as "training data" and/or a "training set" (described further below) to generate an algorithm that will be performed by a computing device/module to produce outputs given data provided as inputs; this is in contrast to a non-machine learning software program where the commands to be executed are determined in advance by a user and written in a programming language. Machine-learning process may utilize supervised, unsupervised, lazy-learning processes and/or neural networks, described further below. As a non-limiting example, proprietary algorithms may be developed utilizing obtained datum and known correlations between physiology, heat transfer, heat stress, and athletic performance. As a non-limiting example, proprietary algorithms may be developed utilizing obtained datum and known correlations between physiology, heat transfer, heat stress, and athletic performance. These algorithms could be used to provide athletes with customized training plans based on their physiological data. By analyzing how an athlete's body responds to heat stress during exercise, for example, trainers could develop a better understanding of how to optimize training regimens. Additionally, these algorithms could be used to monitor athletes' performance during training and competitions, allowing coaches to make real-time adjustments to training plans. The use of proprietary algorithms could also have applications outside of athletics, such as in the field of medicine, where they could be used to analyze patient data and develop personalized treatment plans. In some embodiments, computing device 120 may generate a proprietary algorithm using and/or including a machine-learning model, such as without limitation a classifier configured to receive exercise datum and/or biometric datum 116 and output a propriety algorithm. Categories for classifying the inputs may be predetermined based on exercises datum, for example an outdoor run exercise may include more heat and heart rate related categories, such as heat stress, or may be user selected through a user input. Training data for a proprietary classifier may include elements of exercise datum and biometric datum correlated to a plurality of proprietary categories and a plurality of proprietary metrics of the proprietary categories. A "proprietary category," as used herein, is a health related category to which data may be classified. Health may refer to physiological, athletic, and other categories as described above, such as heat stress. A "proprietary metric," as used herein, is a score categorizing the impact of exercise datum and/or biometric datum. The proprietary metric may be linguistic or numerical. For example, a heart rate range of 120-140 beats per minute nay be scored as "dangerous," "intense," and the like. In some embodiments, proprietary classifier training data may be categorized based on groupings such as age, demographic, geographic location, elements of biometric data 116 and or exercise data, and the like. For example, a proprietary metric for what is a considered a dangerous heart rate for an African American may differ from a national average of the region in which a user lives in. Proprietary algorithms generated may be used as inputs or training for other machine-learning models as described throughout this disclosure. Computing device 120 may us a separate machine learning process to select the training data to train the proprietary classifier based on the data received from as user.

Still referring to FIG. 1, computing device 120 may function as an interface between the user and the ambient environment, increasing the rate and capacity of heat transfer through the system. For example, computing device 120 may instruct a cooling element to increase or decrease the temperature of the glabrous areas of user housing 104 is attached to as a function of biometric datum and/or exercise datum. Computing device 120 may instruct cooling device 108 incrementally cool the housing, which in turn, cools the glabrous area of a user, as a function of the user's excursion, body temperature, blood pressure, exercise datum, and the like. In some embodiments, computing device 120 may control cooling device 108 by controlling the fan speed of a fan connected to a heatsink such as a heatsink fan. For example, computing device 120 may activate a heatsink fan to force air across the heatsink, which may allow more unheated air to move across the heat sink surface and increase the convective cooling of the heatsink. In some embodiments, computing device 120 may control cooling device 108. In some embodiments, computing device 120 may control cooling device 108 by controlling a thermo-electric cooler, such as a Peltier cooler, connected to a heatsink for thermoelectric cooling as described above. Computing device 120 may also operate a thermoelectric cooler. As a non-limiting example, computing device 120 may control thermoelectric cooler as a function biometric datum. As a non-limiting example, computing device 120 may control thermoelectric cooler to increase the temperature difference between the "hot" and "cool" sides of the thermoelectric cooler if biometric datum indicates that more cooling is needed. In some embodiments, computing device 120 may control thermoelectric cooler by changing the voltage applied to the thermoelectric cooler.

Still referring to FIG. 1, computing device 120 may use machine-learning to control cooling element 108 based on biometric datum 116 exceeding a biometric threshold. A "biometric threshold," as used in this disclosure, is a threshold value of biometric datum. For example, a biometric threshold may be based on the temperature of the glabrous area of a user, alone or in combination, with the heart rate of the user. In some embodiments exceeding the biometric threshold, may cause computing device 120 to signal cooling element 108 to transfer heat from a glabrous area of a user. In some embodiments, a biometric threshold may be set by user through a user input. For example, a user may input when their heart rate is below 60 beats per minute to raise the temperature of the glabrous area of the user by transferring heat from housing 104 through cooling element 108 to the glabrous area until their heartbeat is 80 beats per minute. In some embodiments, computing device 120 may calculate the biometric threshold using a lookup table. A "lookup table," as used in this disclosure, is an array of data that maps input values to output values, thereby approximating a mathematical function. Given a set of input values, a lookup operation retrieves the corresponding output values from the table. If the lookup table does not explicitly define the input values, computing device 120 can estimate an output value using interpolation, extrapolation, or rounding, wherein interpolation is a process for estimating values that lie between known data points; extrapolation is a process for estimating values that lie beyond the range of known data points; and a rounding is a process for approximating a value by altering its digits according to a known rule. Additionally, a look table may be applied as training data to machine-learning models as described throughout this disclosure.

Still referring to FIG. 1, in some embodiments, a lookup table may incorporate a wide array of input values. Such values might encompass proprietary metrics/scores, specialized metrics, proprietary algorithms, and detailed reports. Notably, these metrics may extend to, but are not limited to, the quantification of immediate heat stress and overall thermal health. For example, proprietary algorithms generated by the proprietary classified, as described above, may be stored in the look up table. These assessments are primarily grounded in a range of physiological and environmental parameters. Core temperature, both of the skin and the body as a whole, is a pivotal determinant, providing key insights into an individual's thermal state. Blood flow patterns may indicate the body's response to temperature variations. Heat flux, or the rate at which heat energy is transferred across surfaces, provides another layer of understanding, particularly when combined with data regarding the surrounding ambient environment. Furthermore, the gathered data and the resultant scores may have profound implications for health assessments. These scores can be directly correlated with a variety of health conditions and symptoms. For instance, there might be a direct relationship between certain values and the onset of heat illnesses, a spectrum that ranges from mild heat stress to more severe conditions like hyperthermia. On the cooler side of the spectrum, data might signal the advent of hypothermia. Additionally, non-environmental factors, such as physiological responses manifested as hot flashes, general stress, fever, or even the onset of illnesses like influenza, can be discerned based on the metrics. Therefore, this lookup table, by analyzing a blend of environmental and physiological data, offers a comprehensive tool for preempting and diagnosing a broad range of health conditions. In a non-limiting example, consider the metric of cooling efficiency or heat dissipation. This metric within lookup table may offer a quantification of the heat flux passing through apparatus and the user's hands, subsequently providing a score that denotes the efficiency of core cooling. In this context, a higher score would signify a more rapid evacuation of heat from the body. Such a scoring system can have direct implications, prompting either behavioral changes in the user or automated adjustments, may be powered by machine learning algorithms, to apparatus setting in order to boost its performance. The data inputs that contribute to this score may encompass various parameters such as the skin temperature, the temperature of the device, the rate of heat transfer from the human body to the device, and vice versa from the device to the surrounding environment. Additionally, metrics reflecting heat storage in both the human body and the device, as well as the sweat rate, may be integrated.

Still referring to FIG. 1, in embodiments using machine-learning, computing device 120 may use a classifier to calculate the biometric threshold in controlling the transfer of heat by cooling element 108. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 120 and/or another device may generate a classifier using a classification algorithm, defined as a processes whereby a computing device 120 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. A classifier may take user inputs and biometric datum as an input and utilize the training data to calculate the biometric threshold. In some embodiments, training data for a classifier configured to calculate biometric threshold may include example sets of biometric thresholds such as a user's weight, blood pressure, heart rate, and exertion level that would require the computing device 120 to signal cooling element 108 to heat or cool housing 104. For example, an example set may include that a 25 years old male user weighing 230 pounds, with a heart rate higher than 100 beats per minute, and a body temperature of 38 degrees Celsius to remove heat from the glabrous area of akin by cooling housing 104 until the user's heart rate and body temperature reaches what is medically considered average for a 25 year old male user. In some embodiments, the classifier may categorize user inputs received from the user database into efficiency related categories based on the calculated biometric threshold.

Still referring to FIG. 1, computing device 120 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 120 may then calculate a likelihood table by calculating probabilities of different data entries and classification labels. Computing device 120 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 120 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, in some embodiments, computing device 120 may be remote from the housing 104 and be in wireless communication with cooling element 108 through the use of Bluetooth, Wi-Fi, cellular connection, and the like. Computing device may be configured to display the biometric datum, or exercise datum, release of cooling element, temperature datum, and all other datum, disclosed to user through a graphical user interface communicatively connected to computing device 120. A "graphical user interface," as used in this disclosure, is any form of a user interface that allows a user to interface with an electronic device through graphical icons and displays, audio indicators, text-based interface, typed command labels, text navigation, and the like, wherein the interface is configured to provide information to the user and accept input from the user. Computing device 120 may generate a display using a user device, such as a "smartphone", laptop, tablet, internet-of-things (JOT) device, vehicle display, and the like. In embodiments wherein housing 104 is a smartwatch, computing device may display all datum through the smartwatch. For example, computing device 120 may display on a smartwatch face the body temperature of a user. In some embodiments, computing device 120 may also generate improvement datum as a function of exercise datum. "Improvements datum," as used in this disclosure is analytical datum between a user's exercise datum prior to using apparatus 100, while using apparatus 100, and after using apparatus 100. For example, exercise datum may show the improved heartrate/cardiovascular health of a user running while using apparatus 100. In an embodiment, exercise datum may map elucidate the progression in a user's endurance levels or overall performance metrics. For example, with apparatus 100, the user baseline metrics may be established to capture relevant performance effect, such as stamina, strength, agility, and the like. In a non-limiting example, the data may reveal significant enhancements. These might manifest as increased endurance thresholds, improved power output, optimized heart rate levels, or more efficient metabolic rates. Improvement datum may include and or be generated as proprietary metrics/algorithm or any other metric/score evaluation as described in this disclosure. In some embodiments, improvement datum may be generated as the average of metrics regarding exercise datum and/or biometric datum 116 over a period of time. A period of time may be selected by user input, for example, between each use of apparatus 100, between each recorded exercise, between days, weeks, months, and the like. The biometric datum may be generated from user's interaction with graphical user interface may depict a trend of enhanced thermoregulation, allowing for longer, more intense exercise sessions with reduced recovery times. In some embodiments, improvement datum may be fed into machine-learning models as described above as an input, for example, an input into proprietary classifier to generate a new/updated proprietary algorithm including new/updated proprietary metrics. In some embodiments, improvement datum may be applied as training data to machine-learning learning models and/or stored in a look up table as described above.

Figure 2:
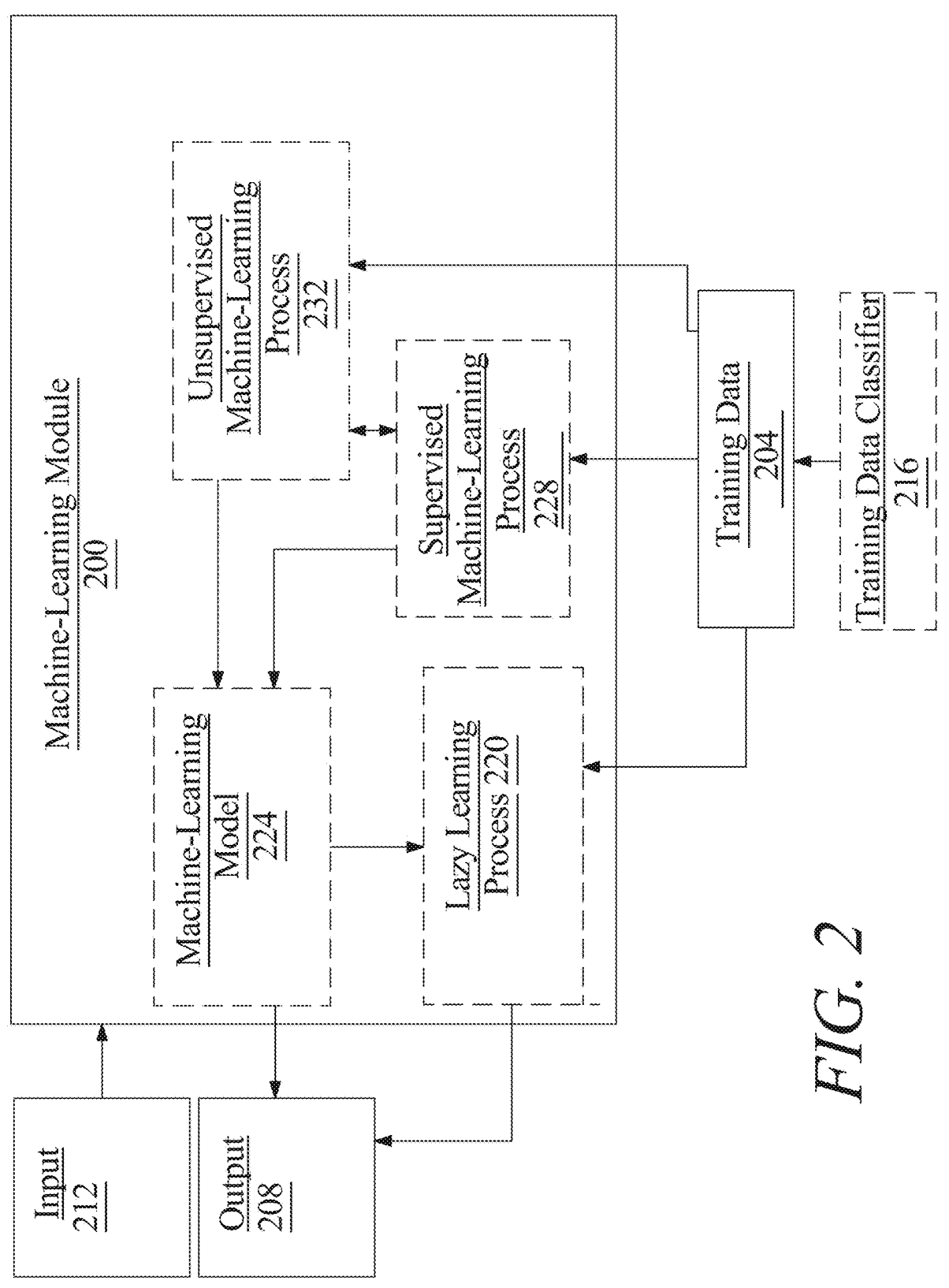
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs, as described above, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the LASSO model is the Frobenius norm amounting to the square root of the sum of squares of all terms. Linear regression models may include the elastic net model, a multi-task elastic net model, a least angle regression model, a LARS LASSO model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Figure 3:
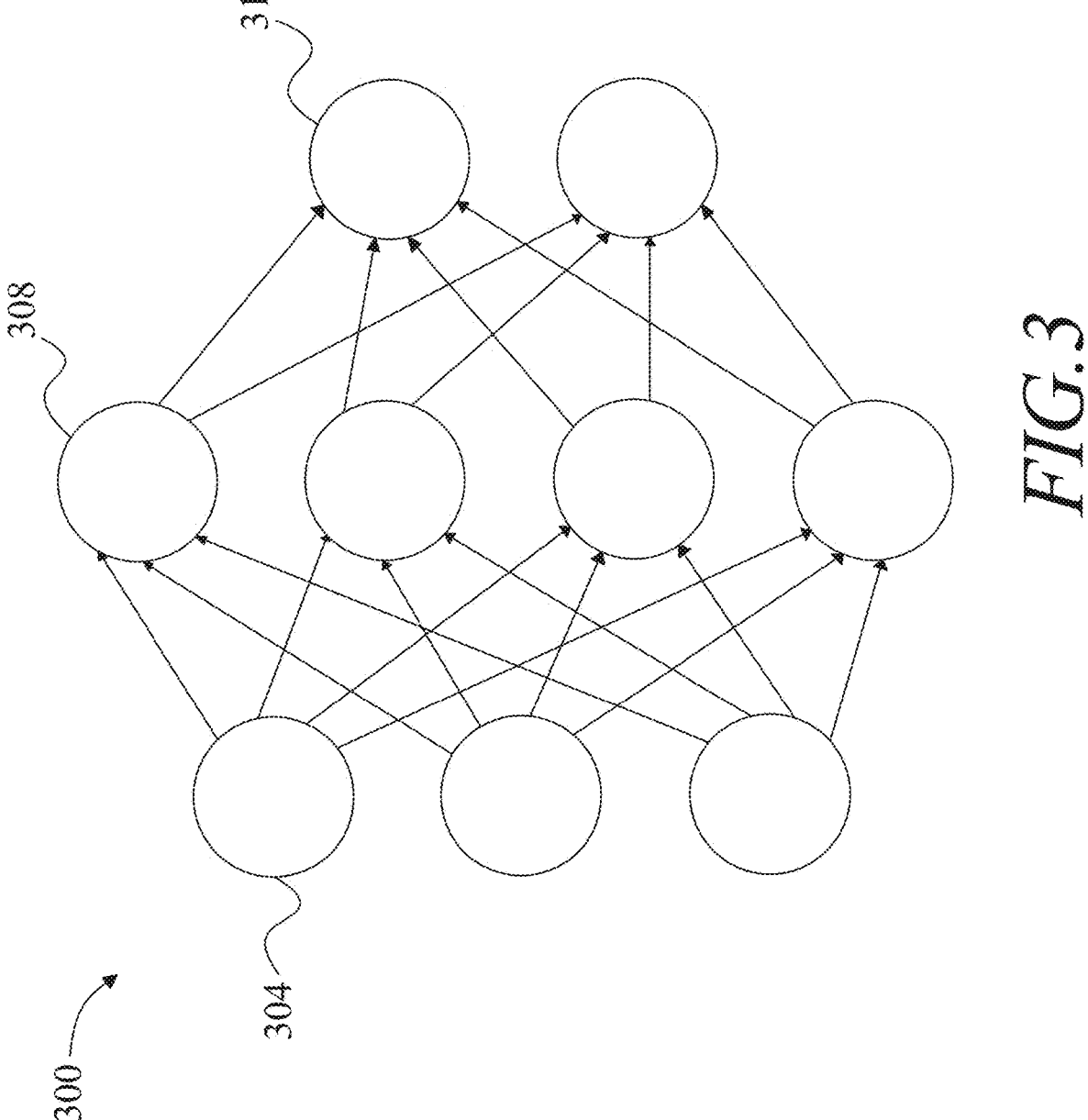
FIG. 3 is a diagram of an exemplary embodiment of neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
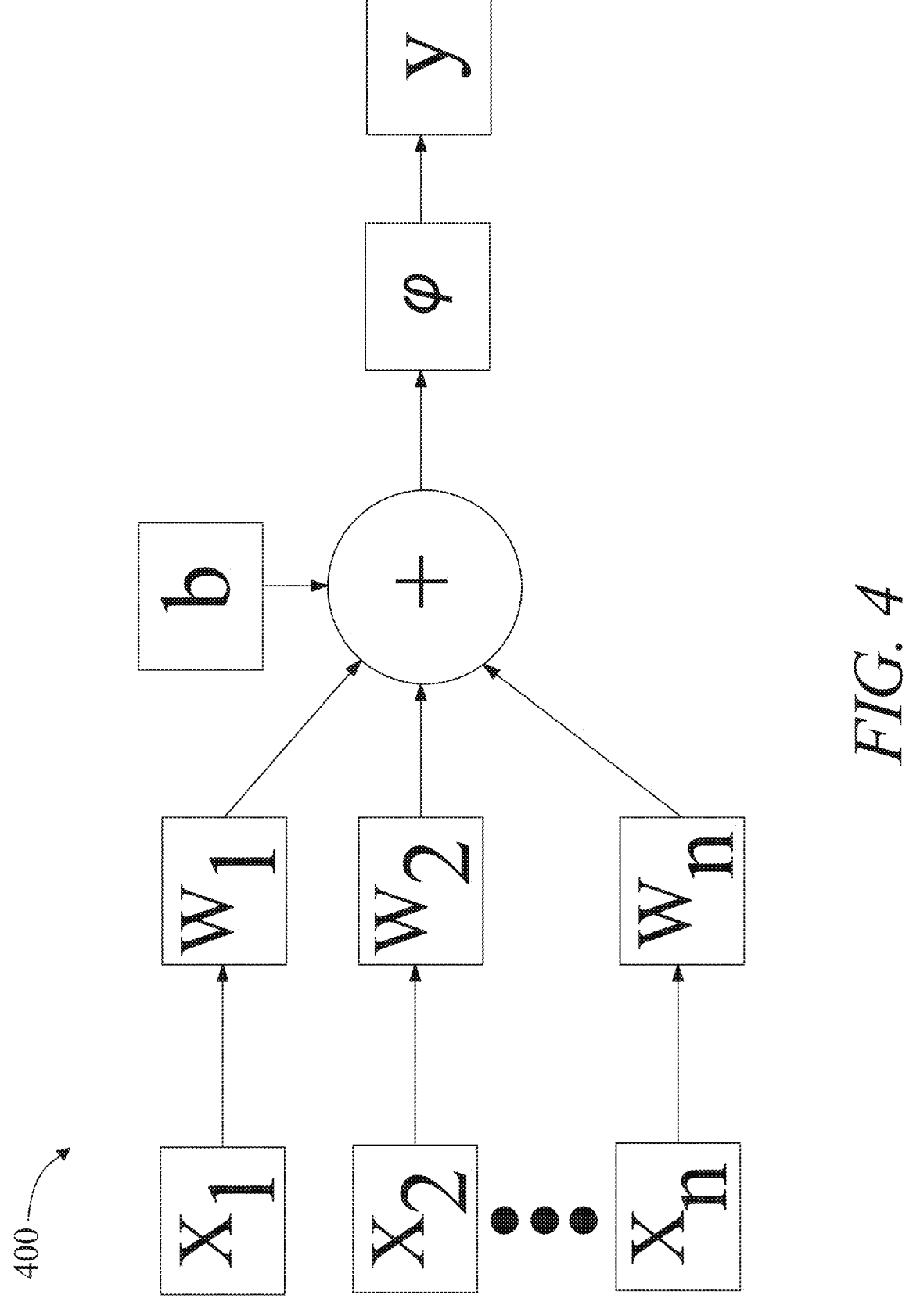
FIG. 4 is a diagram of an exemplary embodiment of a node of a neural network.

Referring now to FIG. 4, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function co, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight.

Referring now to FIG. 5, is an exemplary flow diagram of a method 500 for enhancing physiological thermoregulation. At step 505, method 500 includes placing a housing in contact with a glabrous area of a user, wherein the housing includes a cooling element, and a plurality of sensors configured to generate a biometric datum, for example and with reference to FIG. 1. In some embodiments, the housing includes handwear. The housing may include a nickel exterior. The cooling element may include a plurality of heatsinks. The cooling element may include a copper heat pipe. In some embodiments, the cooling element may include a thermoelectric cooler. In some embodiments, the plurality of sensors may include at least a heat flux sensor. In some embodiments, the biometric datum may include temperature datum relating to the glabrous areas of the user. At step 510, method 500 includes, receiving, by at least a processor communicatively connected to the plurality of sensors, the biometric datum from the plurality of sensors, for example and with reference to FIGS. 1-4. At step 515, method 500 includes controlling, by the at least a processor, the cooling element as a function of the biometric datum, for example and with reference to FIS. 1-4. The processor may be further configured to signal to the cooling element to increase the rate and capacity of heat transfer through the housing as the function of biometric datum. In some embodiments, the processor may use a machine-learning model to calculate a biometric threshold for controlling the cooling element as a function of biometric datum.

Figure 6A:
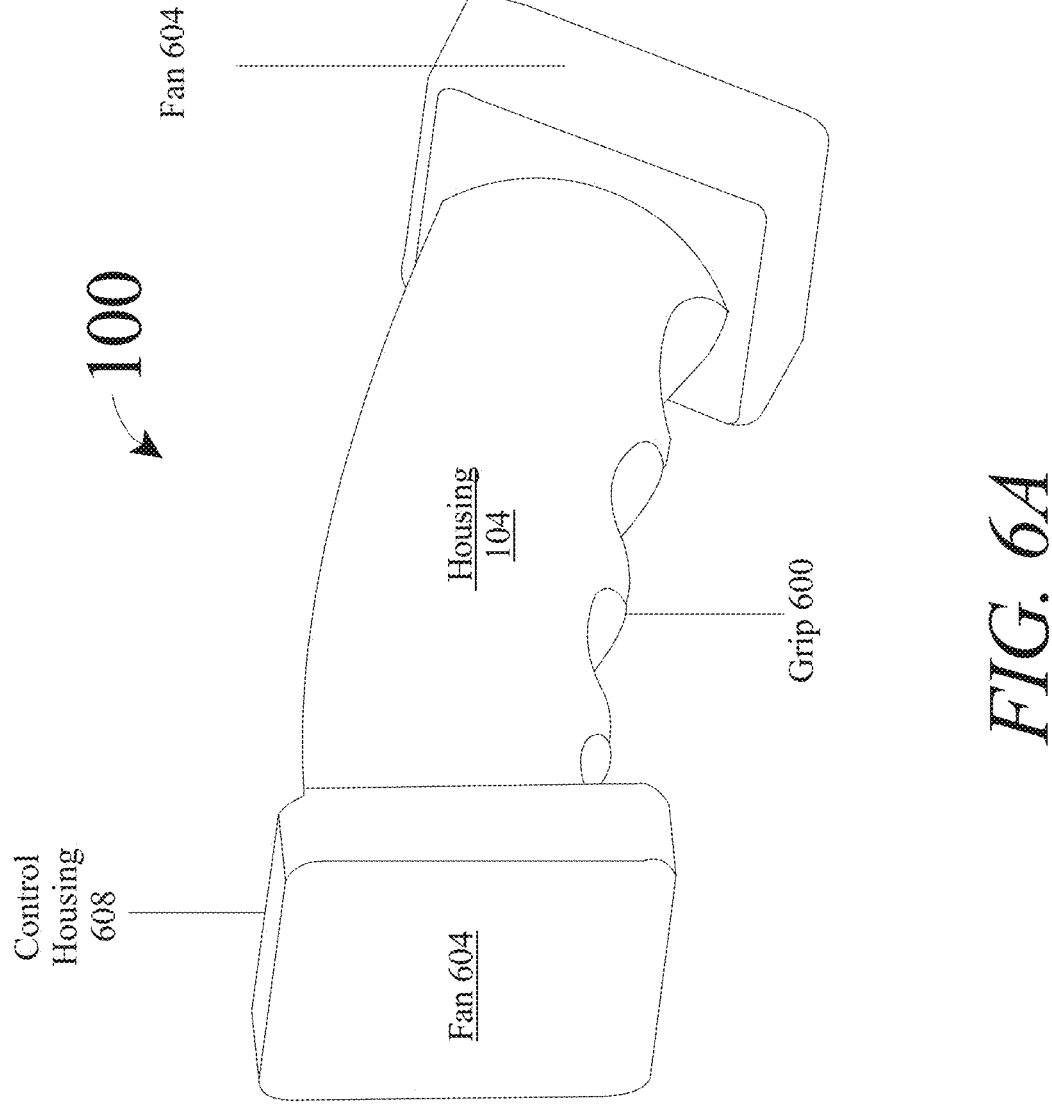
FIG. 6A is an exemplary embodiment of an apparatus for enhancing physiological thermoregulation.

Referring now to FIG. 6A, is an exemplary embodiment of an apparatus 100 for enhancing physiological thermo-regulation is shown. In some embodiments, apparatus 100 may contain an ergonomic housing 104 with a kidney-bean like shape. In some embodiments, housing 104 may include a handle. A "handle" for the purposes of this disclosure, is an object that is adapted to be grasped by a hand. Housing 104 may range from 4-5 inches in length and 1-3 inches in width. In some embodiments, housing 104 may be made from a material having high thermal conductivity. As a non-limiting example, housing 104 may be made from a metal, such as copper or aluminum. As a non-limiting example, housing 104 may be made from carbon fiber, wherein the fibers of the carbon fiber are oriented in the direction that heat needs to be conducted in. In some embodiments, the handle of housing 104 may be disposed between the one or more fans 604. Additionally, housing 104 of housing 104 may include a grip 600. In some embodiments, grip 600 may include a textured portion of housing 104 of housing 104. The textured portion may allow for a user to maintain a hold on apparatus 104 with greater ease. In some embodiments, grip 600 may include grooves along housing 104 to allow a person to easily grip and connect a glabrous area of skin, such as a palm of a hand, to housing 104. In some embodiments, the grooves may be configured and arranged so as to receive human fingers. In some embodiments, apparatus 100 may include one or more fans 604. One or more fans 604 may be affixed to an end of housing 104. In some embodiments, apparatus 100 may include two fans 604, with one on both ends of housing 104 for constant airflow. In some embodiments, fan 604 may be a battery-powered fan. Cool air may enter at one end of housing 104, travel through, and exit at the opposite end of housing 104. in some embodiments, the fans may range from, 1-1.5 inches. In some embodiments, apparatus 100 may contain a control housing 608. A "control housing," as used in this disclosure, is a compartment containing a plurality of devices. For example, housing 104 may contain control housing 608 on a top end of housing 104 as described further below.

Figure 6B:
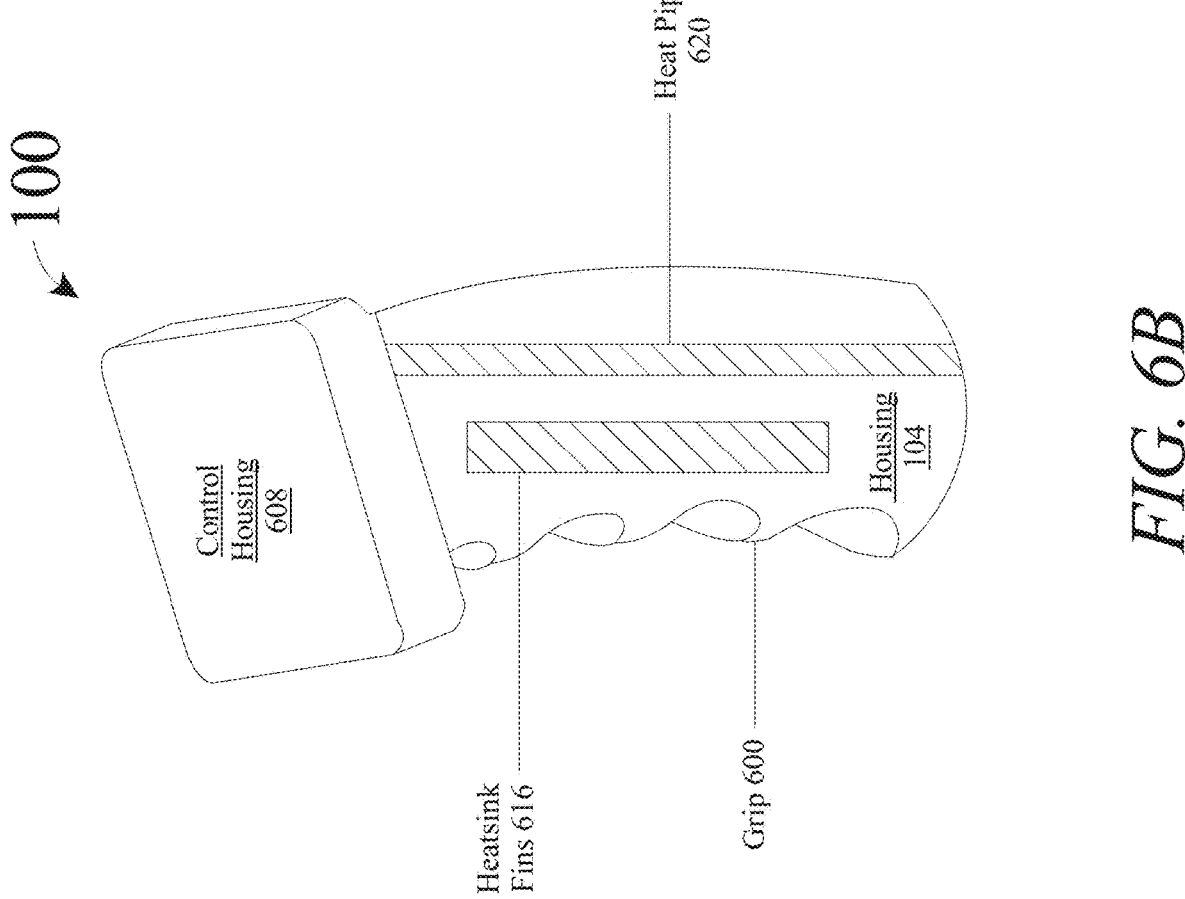
FIG. 6B is an exemplary embodiment of an interior to an apparatus for enhancing physiological thermoregulation.

Referring now to FIG. 6B is an exemplary embodiment of an interior to apparatus 100 for enhancing physiological thermoregulation. Within the interior of housing 104 may be a cooling element 108. For example, cylindrical longitudinal heatsink fins 616 may run throughout the interior of housing 104. In some embodiments, heatsink fins 616 may be arranged radially inside of an aperture in apparatus 100. In some embodiments, aperture may be cylindrically shaped. In some embodiments, aperture may be in fluid communication with fan/fans 604. As a non-limiting example, fan/fans 604 may be configured to draw air through the aperture and over heatsink fins 616; therefore, increasing the convective cool-ing ability of the heatsink fins 616. Additionally, in some embodiments, a heat pipe 620 may also be contained within the interior of housing 104. In some embodiments, heat pipe 620 may be configured to conduct heat from a user to a heatsink. In some embodiments, heat pipe 620 may be a copper heat pipe. Heat pipe 620 may be consistent with any heat pipe discussed as part of this disclosure.

Figure 6C:
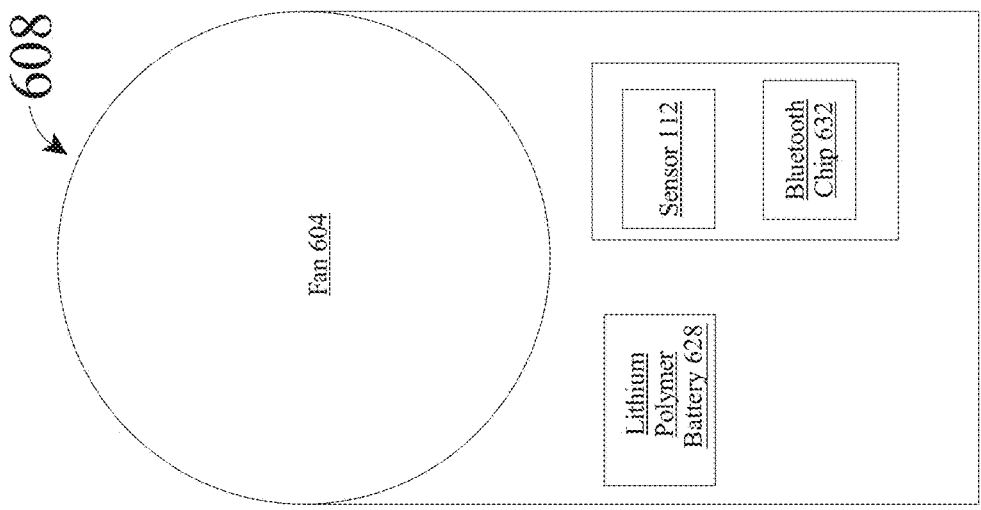
FIG. 6C is an exemplary embodiment of a control housing.

Referring now to FIG. 6C is an exemplary embodiment of a control housing 608. Control housing 608 may contain a sensor 112, such as a flat surface type K thermocouple, lithium polymer battery 628, and a Bluetooth low energy chip 632 in addition to the battery powered fan 604 at one end of hosing 104. Bluetooth low energy chip 632 may allow for apparatus 100 to wirelessly connect with one or more other computing device, such as smartphones, smart-watches, laptops, desktops, smart televisions, and the like.

It is to be noted that any one or more of the aspects and embodiments described herein may be conveniently imple-mented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the imple-mentation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not lim-ited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any com-binations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a com-puting device) and any related information (e.g., data struc-tures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
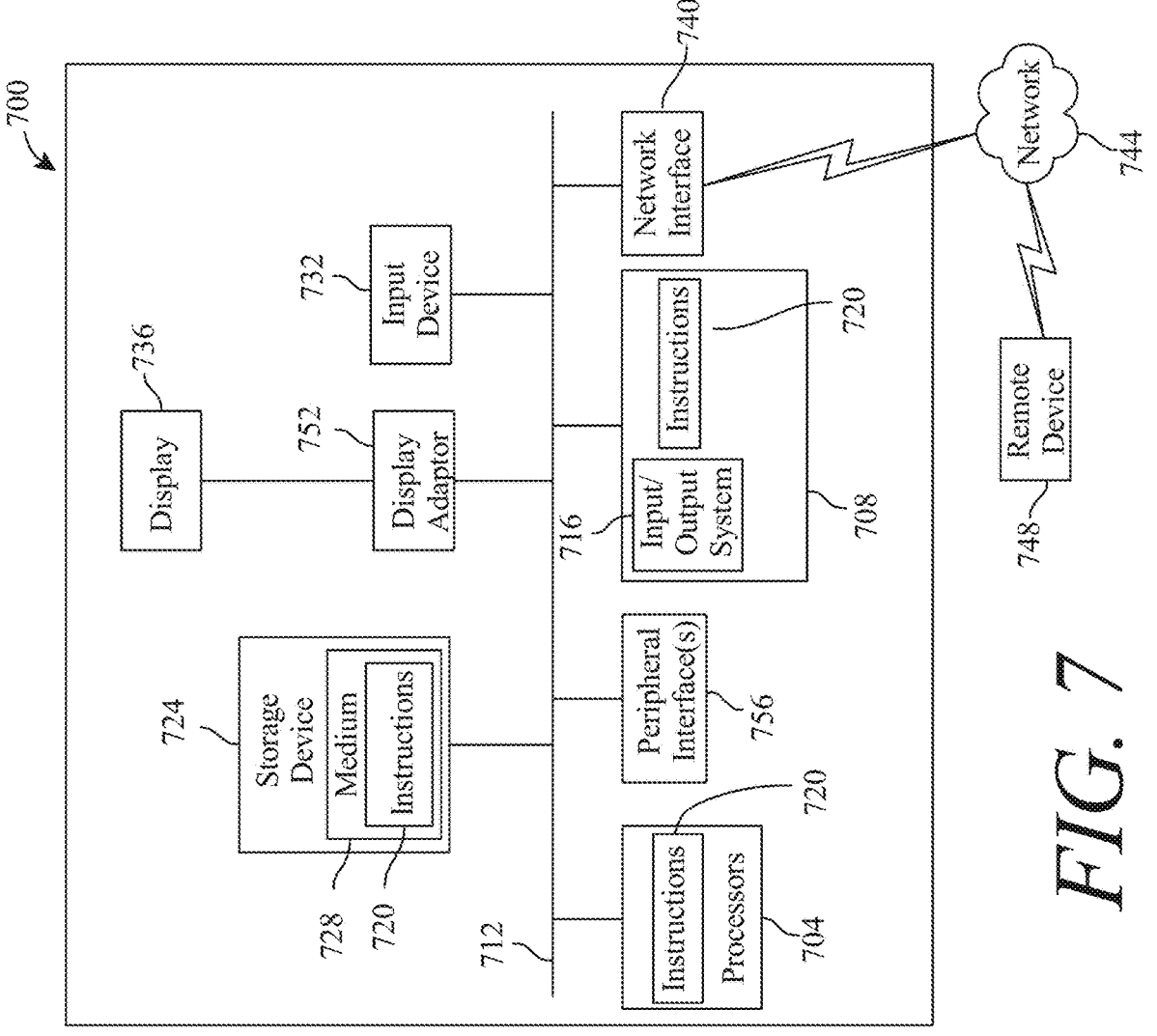
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736 discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, apparatuses, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for enhancing physiological thermoregulation, the apparatus comprising:
   a housing having an ergonomic contour and configured to contact a glabrous area of a hand of a user;
      a cooling element comprising a thermoelectric cooler; and
      a plurality of sensors configured to receive a biometric datum and an initial exercise datum;
   at least a processor communicatively connected to the plurality of sensors; and
   a memory communicatively connected to the at least processor, the memory containing instructions configuring the at least processor to:
      receive the biometric datum and the initial exercise datum from the plurality of sensors;
      determine a biometric threshold using a machine learning model and the biometric datum as an input to the machine learning model;
      control the cooling element as a function of the determined biometric threshold;
      receive a subsect exercise datum from the plurality of sensors; and
      generate an improvement datum based on a subsequent exercise datum.

2. The apparatus of claim 1, wherein the housing comprises handwear.

3. The apparatus of claim 1, wherein the housing comprises an aluminum exterior.

4. The apparatus of claim 1, wherein the cooling element comprises a plurality of heatsinks.

5. The apparatus of claim 1, wherein the plurality of sensors comprises at least a type k thermocouple.

6. The apparatus of claim 1, wherein the biometric datum comprises temperature datum relating to the glabrous areas of the user.

7. The apparatus of claim 1, wherein the memory contains instructions further configuring the processor to send a signal to the cooling element to increase a rate of heat transfer through the housing as the function of biometric datum.

8. The apparatus of claim 1, wherein the exercise datum comprises data related to physical activity of the user.

9. The apparatus of claim 1, wherein the improvement datum comprises an improved biometric calculation based on the subsequent exercise datum.

10. The apparatus of claim 1, wherein generating the improvement datum comprises generating a proprietary algorithm as function of the subsequent exercise datum.

11. A method for enhancing physiological thermoregulation, the method comprising:
   placing a housing in contact with a glabrous area of a user, wherein the housing comprises; a cooling element comprising a thermoelectric cooler; and
      a plurality of sensors configured to receive a biometric datum and an initial exercise datum;
   receiving, by at least a processor, the biometric datum and the initial exercise datum from the plurality of sensors;
   determining, by the at least a processor, a biometric threshold using a machine learning model and the biometric datum as an input to the machine learning model;
   controlling, by the at least a processor, the cooling element as a function of the determined biometric threshold;
   receiving, by the at least a processor, a subsect exercise datum from the plurality of sensors; and
   generating, by the at least a processor, an improvement datum based on a subsequent exercise datum.

12. The method of claim 11, wherein the housing comprises handwear.

13. The method of claim 11, wherein the housing comprises an aluminum exterior.

14. The method of claim 11, wherein the cooling element comprises a plurality of heatsinks.

15. The method of claim 11, wherein the plurality of sensors comprises at least a type k thermocouple.

16. The method of claim 11, wherein the biometric datum comprises temperature datum relating to the glabrous areas of the user.

17. The method of claim 11, wherein controlling the cooling element further comprises configuring the processor to send a signal to the cooling element to increase a rate of heat transfer through the housing as the function of biometric datum.

18. The method of claim 11, wherein the exercise datum comprises data related to physical activity of the user.

19. The method of claim 11, wherein the improvement datum comprises an improved biometric calculation based on the subsequent exercise datum.

20. The method of claim 11, wherein generating the improvement datum comprises generating a proprietary algorithm as function of the subsequent exercise datum.

* * * * *